(12) United States Patent
Velikov et al.

(10) Patent No.: US 8,834,532 B2
(45) Date of Patent: Sep. 16, 2014

(54) PLATE FOR THE TREATMENT OF BONE FRACTURES

(75) Inventors: Jordan Velikov, Thalwil (CH); Simona Paganetto, Winterthur (CH)

(73) Assignee: Zimmer GmbH (CH)

( * ) Notice: Subject to any disclaimer, the term of this patent is extended or adjusted under 35 U.S.C. 154(b) by 193 days.

(21) Appl. No.: 12/683,962

(22) Filed: Jan. 7, 2010

(65) Prior Publication Data

US 2011/0004252 A1   Jan. 6, 2011

(30) Foreign Application Priority Data

Jul. 7, 2009   (EP) .................................... 09008867

(51) Int. Cl.
*A61B 17/80* (2006.01)

(52) U.S. Cl.
CPC ............. *A61B 17/80* (2013.01); *A61B 17/8061* (2013.01)
USPC ............................... 606/280; 606/70; 606/71

(58) Field of Classification Search
USPC .............. 606/280–299, 70, 71, 903, 905, 906
See application file for complete search history.

(56) References Cited

U.S. PATENT DOCUMENTS

| | | | |
|---|---|---|---|
| 4,429,690 A * | 2/1984 | Angelino-Pievani | ......... 606/280 |
| 4,524,765 A | 6/1985 | de Zbikowski | |
| 4,549,540 A | 10/1985 | Caspari et al. | |
| 4,573,458 A | 3/1986 | Lower | |
| 4,776,330 A | 10/1988 | Chapman et al. | |
| 4,838,252 A | 6/1989 | Klaue | |
| 4,867,144 A | 9/1989 | Karas et al. | |
| 4,903,691 A | 2/1990 | Heinl | |
| 4,905,679 A | 3/1990 | Morgan | |
| 4,913,413 A | 4/1990 | Raab | |
| 5,002,544 A | 3/1991 | Klaue et al. | |
| 5,006,120 A | 4/1991 | Carter | |
| 5,015,248 A | 5/1991 | Burstein et al. | |
| 5,041,114 A | 8/1991 | Chapman et al. | |
| 5,053,036 A | 10/1991 | Perren et al. | |
| 5,151,103 A | 9/1992 | Tepic et al. | |
| 5,364,398 A | 11/1994 | Chapman et al. | |
| 5,403,319 A | 4/1995 | Matsen, III et al. | |

(Continued)

FOREIGN PATENT DOCUMENTS

DE   8213228 U1   8/1982
DE   8628766 U1   12/1986

(Continued)

OTHER PUBLICATIONS

Written Opinion of International Application No. PCT/EP2005/052751.

(Continued)

*Primary Examiner* — Matthew Lawson
*Assistant Examiner* — Si Ming Lee
(74) *Attorney, Agent, or Firm* — Schwegman, Lundberg & Woessner, P.A.

(57) ABSTRACT

A plate is provided for the treatment of bone fractures, the plate having a first surface and a second surface, the second surface being opposed to the first surface and being adapted to face a bone surface. At least one of the first and second surfaces defines at least one generally linearly shaped portion of a boundary of at least one cross section of the plate.

24 Claims, 6 Drawing Sheets

(56) References Cited

U.S. PATENT DOCUMENTS

| | | | |
|---|---|---|---|
| 5,437,672 A * | 8/1995 | Alleyne | 606/279 |
| 5,462,547 A | 10/1995 | Weigum | |
| 5,601,553 A | 2/1997 | Trebing et al. | |
| 5,709,686 A | 1/1998 | Talos et al. | |
| 5,718,705 A | 2/1998 | Sammarco | |
| 5,772,662 A | 6/1998 | Chapman et al. | |
| 5,807,396 A | 9/1998 | Raveh | |
| 5,810,823 A | 9/1998 | Klaue et al. | |
| D402,032 S | 12/1998 | Stone | |
| 5,871,018 A | 2/1999 | Delp et al. | |
| 5,938,664 A | 8/1999 | Winquist et al. | |
| 6,093,201 A * | 7/2000 | Cooper et al. | 606/232 |
| 6,096,040 A * | 8/2000 | Esser | 606/280 |
| D443,060 S | 5/2001 | Benirschke et al. | |
| 6,283,969 B1 | 9/2001 | Grusin et al. | |
| 6,309,393 B1 | 10/2001 | Tepic et al. | |
| 6,348,052 B1 | 2/2002 | Sammarco | |
| 6,364,882 B1 | 4/2002 | Orbay | |
| D458,374 S | 6/2002 | Bryant et al. | |
| D458,683 S | 6/2002 | Bryant et al. | |
| D458,684 S | 6/2002 | Bryant et al. | |
| D458,996 S | 6/2002 | Bryant et al. | |
| D463,557 S | 9/2002 | Bryant et al. | |
| D463,558 S | 9/2002 | Bryant et al. | |
| D463,559 S | 9/2002 | Bryant et al. | |
| 6,454,770 B1 | 9/2002 | Klaue | |
| D464,136 S | 10/2002 | Bryant et al. | |
| D464,731 S | 10/2002 | Bryant et al. | |
| D469,532 S | 1/2003 | Bryant et al. | |
| D469,533 S | 1/2003 | Bryant et al. | |
| D469,534 S | 1/2003 | Bryant et al. | |
| 6,506,191 B1 | 1/2003 | Joos | |
| D469,874 S | 2/2003 | Bryant et al. | |
| D469,875 S | 2/2003 | Bryant et al. | |
| D470,588 S | 2/2003 | Bryant et al. | |
| D479,331 S | 9/2003 | Pike et al. | |
| 6,623,486 B1 | 9/2003 | Weaver et al. | |
| 6,645,208 B2 | 11/2003 | Apfelbaum et al. | |
| 6,712,820 B2 | 3/2004 | Orbay | |
| 6,755,832 B2 | 6/2004 | Happonen et al. | |
| 6,786,909 B1 * | 9/2004 | Dransfeld et al. | 606/283 |
| 6,821,278 B2 | 11/2004 | Frigg et al. | |
| 6,866,665 B2 | 3/2005 | Orbay | |
| D505,205 S | 5/2005 | Freid | |
| 6,890,335 B2 | 5/2005 | Grabowski et al. | |
| D520,637 S | 5/2006 | Kay et al. | |
| 7,052,499 B2 | 5/2006 | Steger et al. | |
| 7,128,744 B2 | 10/2006 | Weaver et al. | |
| D536,453 S | 2/2007 | Young et al. | |
| 7,318,825 B2 | 1/2008 | Butler et al. | |
| 7,341,589 B2 | 3/2008 | Weaver et al. | |
| D576,731 S | 9/2008 | Strnad et al. | |
| D580,056 S | 11/2008 | Orthner | |
| D580,057 S | 11/2008 | Ramadani | |
| 7,479,143 B2 | 1/2009 | Suh et al. | |
| D594,123 S | 6/2009 | Haidukewych et al. | |
| 7,648,508 B2 | 1/2010 | Lutz et al. | |
| 8,246,664 B2 * | 8/2012 | Terrill et al. | 606/286 |
| 2002/0188296 A1 | 12/2002 | Michelson | |
| 2003/0130665 A1 | 7/2003 | Pinczewski et al. | |
| 2004/0097937 A1 * | 5/2004 | Pike et al. | 606/69 |
| 2004/0102775 A1 | 5/2004 | Huebner | |
| 2004/0111183 A1 | 6/2004 | Sutherland | |
| 2004/0116930 A1 | 6/2004 | O'Driscoll et al. | |
| 2004/0153073 A1 | 8/2004 | Orbay | |
| 2004/0220572 A1 | 11/2004 | Michelson | |
| 2004/0225291 A1 * | 11/2004 | Schwammberger et al. | 606/71 |
| 2005/0049595 A1 | 3/2005 | Suh et al. | |
| 2005/0090825 A1 | 4/2005 | Pfefferle et al. | |
| 2006/0173458 A1 * | 8/2006 | Forstein et al. | 606/69 |
| 2006/0217722 A1 | 9/2006 | Dutoit et al. | |
| 2006/0235402 A1 | 10/2006 | Celli et al. | |
| 2006/0241607 A1 | 10/2006 | Myerson et al. | |
| 2007/0055253 A1 | 3/2007 | Orbay et al. | |
| 2007/0239163 A1 | 10/2007 | Strnad et al. | |
| 2007/0270853 A1 * | 11/2007 | Leung | 606/69 |
| 2008/0021477 A1 | 1/2008 | Strnad et al. | |
| 2008/0051786 A1 * | 2/2008 | Jensen | 606/61 |
| 2008/0132960 A1 | 6/2008 | Weaver et al. | |
| 2008/0183172 A1 | 7/2008 | Fritzinger | |
| 2008/0200955 A1 | 8/2008 | Tepic | |
| 2008/0234676 A1 | 9/2008 | Schulze et al. | |
| 2008/0300637 A1 | 12/2008 | Austin et al. | |
| 2009/0018587 A1 | 1/2009 | Bottlang | |
| 2009/0024171 A1 * | 1/2009 | Leone | 606/280 |
| 2009/0318920 A1 | 12/2009 | Jacobs | |
| 2010/0234896 A1 | 9/2010 | Lorenz et al. | |

FOREIGN PATENT DOCUMENTS

| | | |
|---|---|---|
| EP | 0515828 A1 | 12/1992 |
| EP | 0934731 A1 | 8/1999 |
| EP | 1477124 A1 | 11/2004 |
| FR | 2405062 A1 | 5/1979 |
| FR | 2405706 A1 | 5/1979 |
| FR | 2517536 A1 | 6/1983 |
| FR | 2517536 A1 | 6/1983 |
| JP | 11299804 A | 11/1999 |
| WO | WO99/38448 A1 | 8/1999 |
| WO | WO2004/089233 A1 | 10/2004 |
| WO | WO2005/122916 A1 | 12/2005 |
| WO | WO2007/006430 A1 | 1/2007 |
| WO | WO2007/138062 A1 | 6/2007 |
| WO | WO2007/137437 A2 | 12/2007 |
| WO | WO-2007138062 A1 | 12/2007 |
| WO | WO2008/019511 A1 | 2/2008 |
| WO | WO2009/009521 A2 | 1/2009 |
| WO | WO2011/004266 A1 | 1/2011 |

OTHER PUBLICATIONS

International Preliminary Examination Report issued Oct. 6, 2006 in International Application No. PCT/EP2005/052751.
Kienzle et al. "Total Knee Replacement" IEEE Engineering in Medicine and Biology Magazine, New York, vol. 14, No. 3, May 1, 1995, pp. 301-306.
Intrauma, Periprosthetics, Product Brochure, Feb. 2010.
LaPlaque Femoral Anatomique, Lefevre et al., Maitrise Orthopedique No. 164, May 2007.
Synthes DHS/DCS System Including LCP DHS and DHS Blade, Technique Guide, Synthes 2007.
Synthes Distal Femur Plates. Shape Based on Distal Femur LISS Plate Design, Product Brochure, Synthes Inc. 2007.
Synthes Locking Attachment Plate. For Treatment of Periprosthetic Fractures, Technique Guide, Synthes Inc. Dec. 2009.
Synthes Locking Compression Plate (LCP) System. Locking Screw Technology and Conventional Plating in one System, Product Brochure, Synthes Inc. 2003.
Synthes Trochanter Stabilization Plate for DHS, Technique Guide, Synthes USA 2000.
Synthes Universal Locking Trochanter Stabilization Plate (ULTSP). For Use with the DHS/DCS and LCP DHHS Systems, Technique Guide, Synthes Inc. 2007.
Product Brochure—Zimmer NCB Plating System, A locking plate system that expands a surgeon's options in trauma surgery, 97-2370-001-00 5 ML, 2006 Zimmer, Inc.
Surgical Technique—Zimmer NCB Distal Femoral Plating System, The right locking option for tough fractures.
"International Application Serial No. PCT/IB2010/001995, International Preliminary Report on Patentability mailed Jan. 10, 2012", 5 pgs.
"International Application Serial No. PCT/IB2010/001995, International Search Report mailed Nov. 5, 2010", 4 pgs.
"International Application Serial No. PCT/IB2010/001995, Written Opinion mailed Nov. 5, 2010", 4 pgs.

* cited by examiner

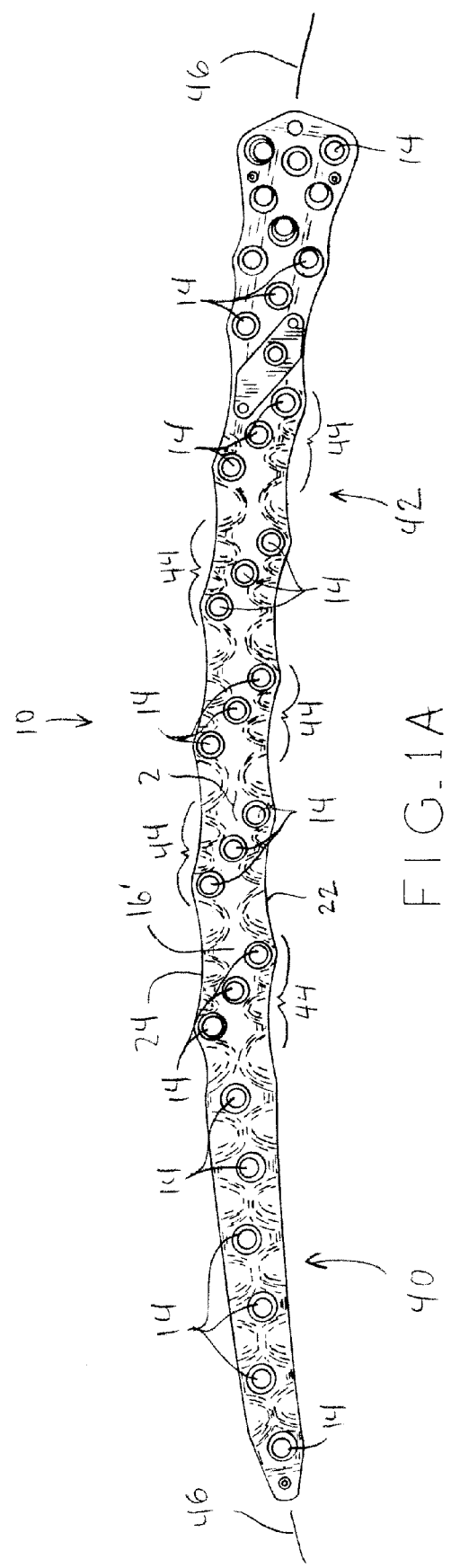

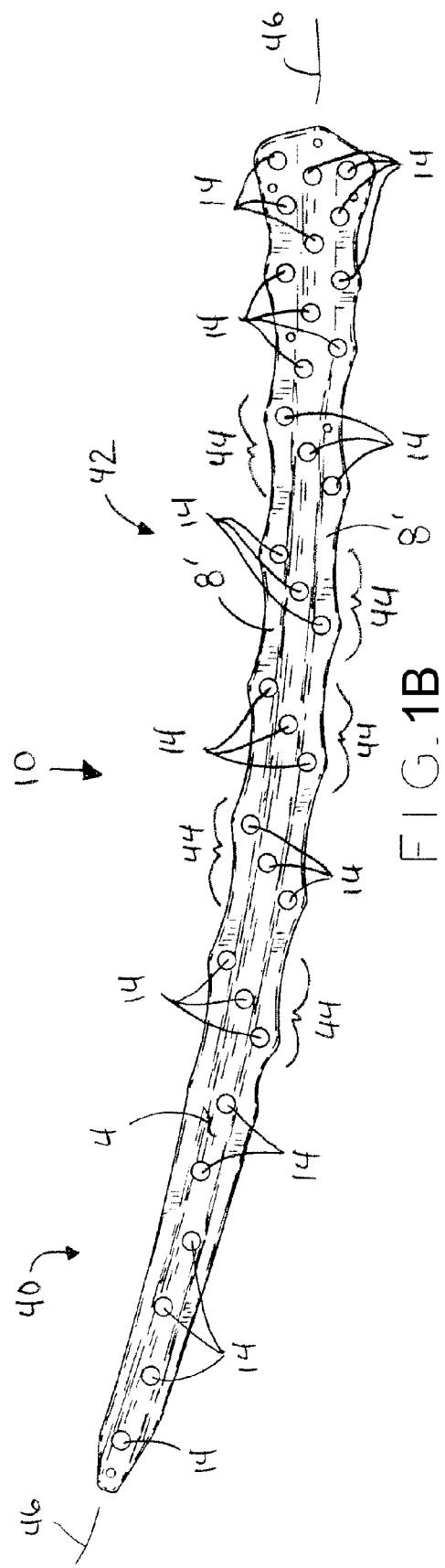

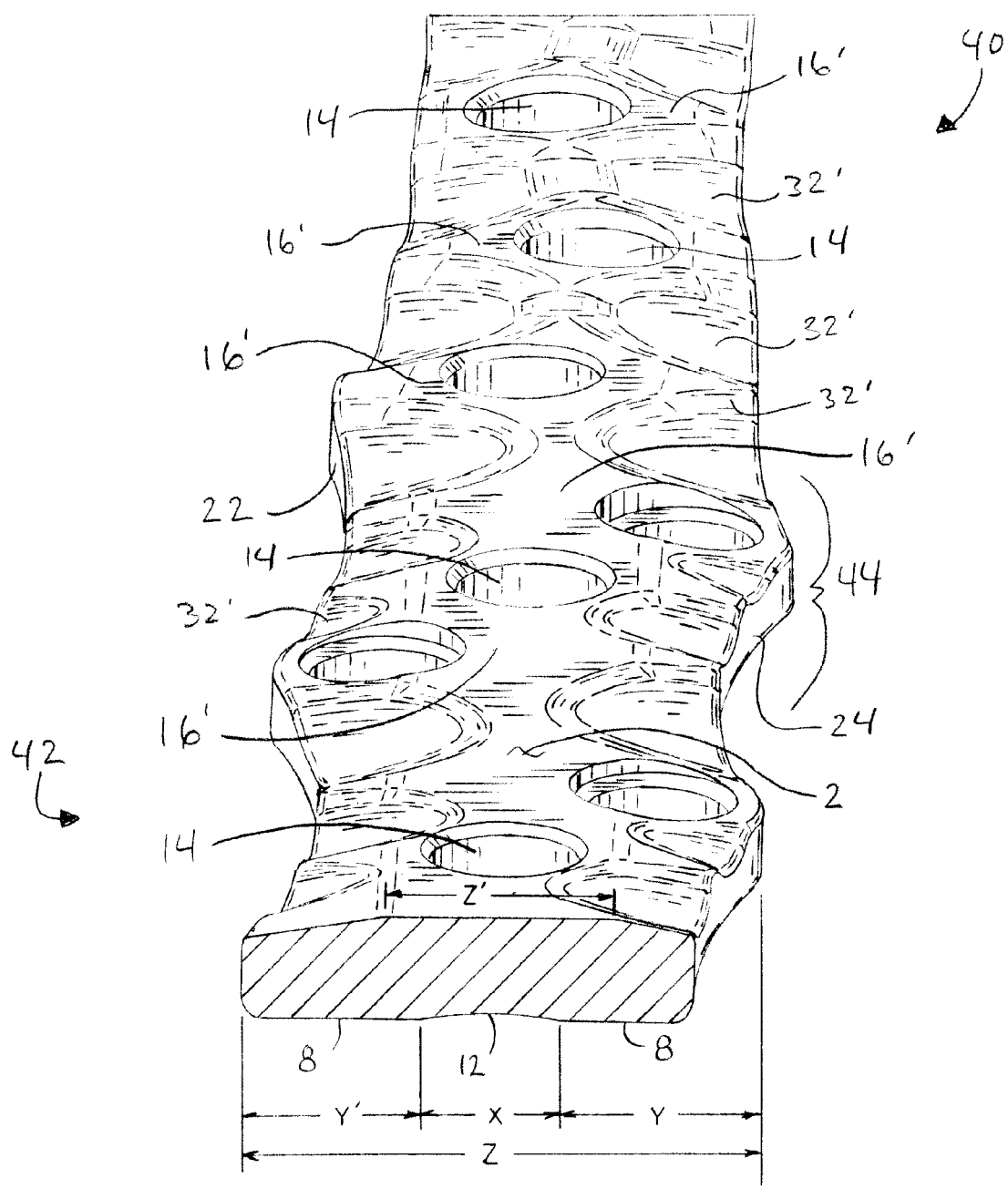
FIG_6

PLATE FOR THE TREATMENT OF BONE FRACTURES

CROSS-REFERENCE TO RELATED APPLICATIONS

This application claims priority from European Patent Application No. EP09008867.5, filed Jul. 7, 2009, the disclosure of which is hereby expressly incorporated by reference herein in its entirety.

BACKGROUND

1. Field of the Disclosure

The present disclosure relates to a plate for the treatment of bone fractures.

2. Description of the Related Art

To aid the treatment and healing process of fractured bones, it is known to use plates, screws, pins and wire cerclages as internal fixation means. For complicated fractures the bone and the bone fragments have to be fixated securely by use of plates. However, a stiff plate increases the risk of mal-union or non-union due to the stress-shielding effect.

To reduce the risk of mal-union or non-union due to the stress-shielding effect, one has to reduce the stiffness of the plate. However, this reduces the strength of the plate and in some cases can lead to fatigue failure of the plate. Thus a plate for the treatment of bone fractures with an ideal ratio between the strength and the stiffness of the metal plate is desired. In addition to other advantageous properties, the subject matter described in the claims can also satisfy these demands.

SUMMARY

The plate for the treatment of bone fractures has a first surface and a second surface. The second surface is opposed to the first surface and is adapted and suited to face a bone surface, with at least one of the first and second surfaces defining at least one generally linearly shaped portion of a boundary of at least one cross section of the plate.

Conventional plates used in osteosynthesis typically have a cross-section formed by two concentric radii. In contrast to this cross-section, the plate of the present disclosure has an increased strength and a lower stiffness for a given thickness and width as compared to a conventional circle segmented design. The increased strength has the advantage that it reduces the probability of fatigue failure of the plate, and the reduced stiffness advantageously reduces the risk of mal-union or non-union due to the stress-shielding effect. The fact that the second surface is adapted and suited to facing the surface of the bone at the fracture site enables a more secure fixation of the plate at the fracture site. Moreover, the manufacturing process is improved, as the conventional cross-section having two concentric radii is more costly and work intensive.

In a further aspect, the boundary of the cross section of the plate defines the longer sides of a rectangle within which the boundary of the cross section is inscribed, the second surface defining a non-linearly shaped middle portion which lies inside the rectangle and which is positioned between two generally linearly shaped lateral portions forming a part of one of the longer sides of the rectangle, and the first surface defining a middle portion which forms a part of the other longer side of the rectangle and which is positioned between two lateral portions lying inside the rectangle.

This is particularly advantageous in practice, as a rectangular cross-section has an increased strength and lower stiffness for the same thickness and width as a conventional circle segmented design. This reduces the probability of fatigue failure of the plate and reduces the risk of mal-union or non-union. Also, using a rectangular bar as raw material further reduces the cost of manufacture of the bone fracture plate.

In an aspect of the plate for the treatment of bone fractures, the plate defines a plane and the at least one generally linearly shaped portion is parallel to this plane. Advantageously, the plate can be manufactured from a section of raw material, either in a press or in other suitable machines, reducing the cost of manufacture of the plate.

In a further aspect, the plate has at least one generally linearly shaped portion which is adjacent to at least one non-linearly shaped portion. This is particularly advantageous during the fixation of the plate to the bone, as a flat surface is more firmly held in place, such as by tools, as compared to a non-flat surface.

In another aspect of the plate, the non-linearly shaped portion defines a generally concave or a generally convex part of the boundary of the cross section. This is particularly advantageous, as a generally convex or generally concave non-linearly shaped portion can be easily manufactured by providing either a convex cut out in a generally rectangular bar or by cutting concave parts from a rectangular bar of raw material.

In a further aspect, the non-linearly shaped portion is curved, and in particular has the shape of a circular arc. This is particularly advantageous during the manufacture of the plate, as most cutting and forming tools are adapted to produce circular surfaces and/or cut outs. Moreover, curved surfaces are particularly advantageous as they help to prevent the tissue surrounding the bone at the fracture site from being damaged which shortens the healing time and increases the well being of the patient after surgery.

In an even further aspect of the plate for the treatment of bone fractures, the non-linearly shaped middle portion which is defined by the second surface is adapted to be matched to a contour of the bone surface. This has the advantage that the placement of the second surface onto the bone surface during surgery is enhanced and therefore provides improved attachment of the plate to the bone surface.

In a further aspect of the present disclosure, the first surface of the plate is of generally convex shape. This advantageously provides the plate of the present disclosure with sufficient thickness and, therefore, with sufficient strength.

In a further aspect of the plate of the present disclosure, the first surface defines a generally linearly shaped middle portion. During surgery this has the advantage that it facilitates the use of tools to hold the plate in situ during surgery to improve the attachment of the plate to the bone surface.

In a further aspect of the plate for the treatment of bone fractures, the generally linearly shaped middle portion defined by the first surface is essentially parallel to the generally linearly shaped lateral portions of the second surface. This is particularly advantageous as this leads to an increased strength for a reduction in stiffness, and prevents fatigue failure of the plate used in osteosynthetic surgical procedures. Moreover, the tools used to attach the plate to the bone surface are easier to use, thereby improving the attachment of the plate to the bone and consequently improving the healing process and comfort of the patient during the same.

In a further aspect of the plate, the lateral portions defined by the first surface are curved or generally linearly shaped in the cross section of the plate. These curved or generally linearly shaped portions are easy to manufacture, and they help prevent damage to the tissue at the site of the bone plate.

In a further aspect, the plate has an elongated shape defining a longitudinal extent. Moreover, the cross section of the plate is generally perpendicular to the longitudinal extent. Thus the cross section of the plate is generally perpendicular to the bone surface at every point along the length of the plate. This is particularly useful, as the cross-section of a bone can vary significantly along the longitudinal length of the bone and has a generally bigger cross-section at the end of the bone compared to the generally thinner cross-section of the central part of the bone, thus the generally non-planar shaped middle part of the plate can have different sized cross-sections along the length of the bone.

In a further aspect of the plate, along the longitudinal extent at substantially every cross section of the plate, at least one of the first and second surfaces defines at least one generally linearly shaped portion. Thus, the generally rectangular cross section of the plate is maintained for substantially every section of the plate.

In a further aspect of the present disclosure, the longitudinal extent of the plate is non-linear. This is particularly advantageous if the bone to be fixed is not straight but curved. Moreover, as the cross-section of a bone varies significantly along the longitudinal length of the bone and has a generally bigger cross-section at the end of the bone compared to the generally thinner cross-section of the central part of the bone, the generally non-linearly shaped longitudinal extent of the plate can have different sized cross-sections along the length of the bone. This is advantageously achieved by having a bone plate which extends non-linearly along the surface of the bone.

In a further aspect of the present disclosure at least one hole for a bone screw is provided in the plate extending between the first surface and the second surface, with the bone screw being adapted for fixing the plate to the bone. This leads to an improved attachment means for the bone plate to the bone, and depending on the size of the fracture, and/or the number of fractured bone segments aids the healing process advantageously.

The different aspects described above of the plate in accordance with the independent claim and the features realized there can naturally be combined with one another.

Further aspects of the disclosure are also recited in the dependent claims, the description and the drawings.

Further areas of applicability of the present disclosure will become apparent from the detailed description provided hereinafter. It should be understood that the detailed description and specific examples are intended for the purpose of illustration only and are not intended to limit the scope of the disclosure in any way.

BRIEF DESCRIPTION OF THE DRAWINGS

The present disclosure will be explained in more detail and become fully understood from the detailed description and the accompanying drawings, wherein

FIG. 1A is a top plan view of the plate shown in FIG. 1;

FIG. 1B is a bottom plan view of the plate shown in FIG. 1;

FIG. 6 is a perspective, cross-sectional view of the plate shown in FIG. 1, illustrating a head portion of the plate.

The following description of the embodiments is merely exemplary in nature and is in no way intended to limit the disclosure, its application, or uses.

DETAILED DESCRIPTION

Figure 1:
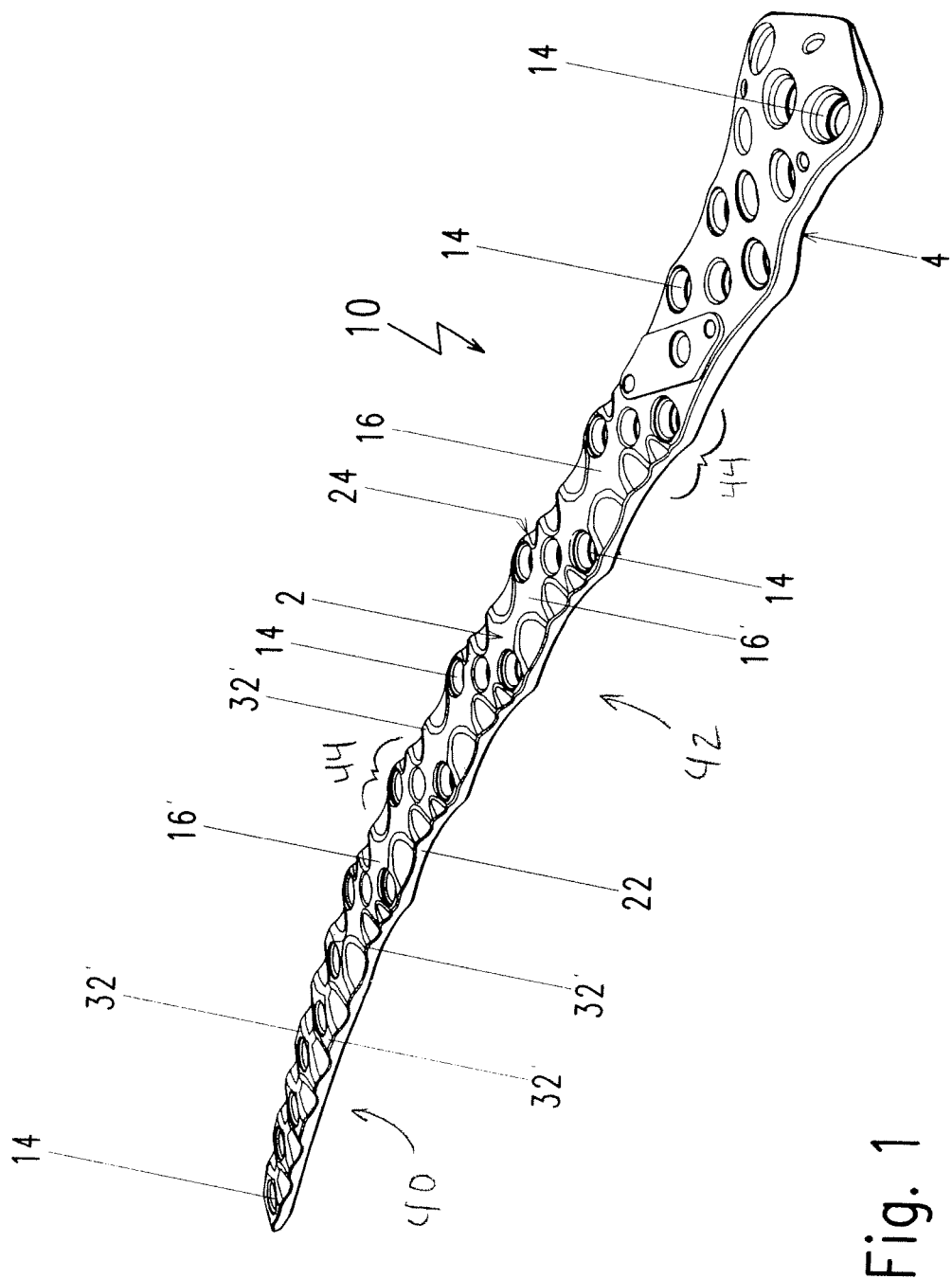
FIG. 1 shows a perspective view of an embodiment of a distal femur plate.
Figure 2:
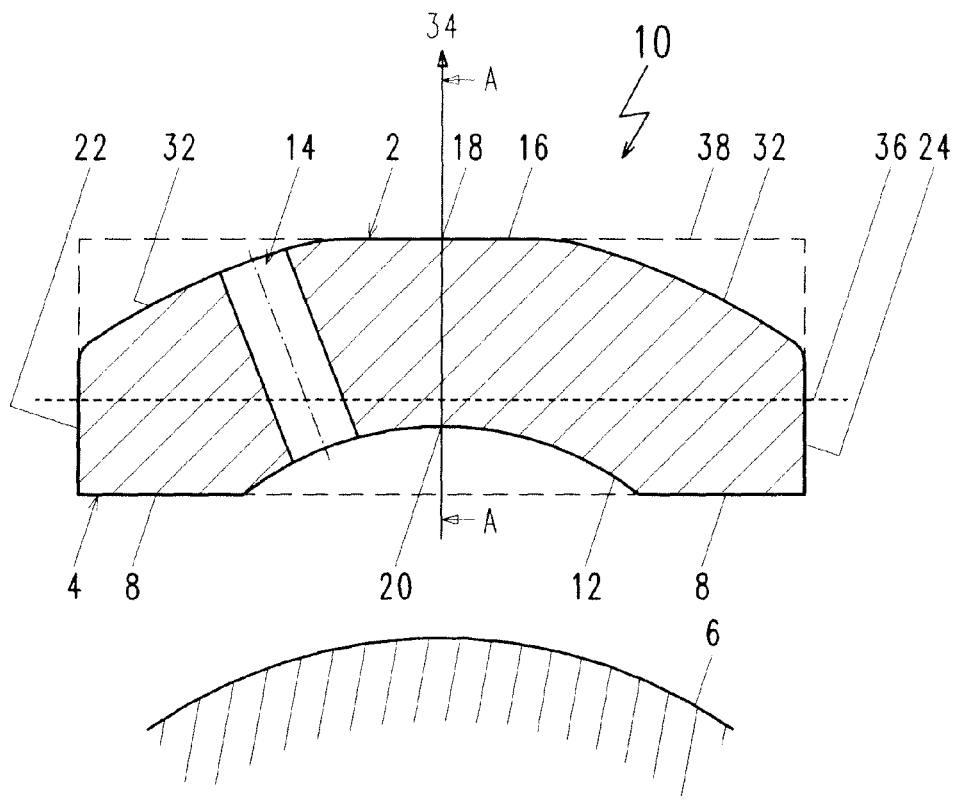
FIG. 2 shows a section of a plate.

FIG. 1 shows a plate, such as distal femur plate 10 to be attached to fractured thigh bone surface 6 (FIG. 2). First or top surface 2 has a plurality of holes 14 and a plurality of portions 16' which—when seen in cross section as explained below—define generally linearly shaped or planar portions 16' and whose respective width varies along the length of plate 10 in accordance with the size and the shape of the bone. Moreover, a plurality of portions 32' are provided which—when seen in cross section as explained below—define different non-linearly shaped or non-planar portions 32'. Holes 14 shown in top surface 2 of plate 10 extend through to second surface 4 which is also known as the bone facing surface 4 or a bottom surface 4. Holes 14 are ideally used in connection with bone screws, which are adapted to fix plate 10 to bone surface 6.

In the following the same reference numerals are used for like features, such as features that are either similar in design or fulfill the same technical function. FIG. 2 shows a cross section of plate 10 in accordance with the present disclosure facing bone surface 6. Bottom surface 4 of plate 10, has a generally non-linearly shaped middle portion 12, which is adapted and suited to be shaped in accordance with the contour of bone surface 6, in this example lying underneath.

Referring to FIG. 2, adjacent to the generally non-linearly shaped middle portion 12, are generally linearly shaped lateral portions 8, which, in this example, are generally perpendicular to sidewalls 22 and 24 of the plate 10. The edges where the generally linearly shaped lateral portions 8 and the sidewalls 22, 24 adjoin, can be rounded, or ground off, or of any shape which prevents damage to the tissue surrounding the bone surface 6 and is preferably easy to manufacture. The generally linearly shaped outer portions 8 and the side walls 22, 24 are generally perpendicular to one another so that the cross-section of plate 10 defines rectangle 38 with two generally linearly shaped portions 8 forming a part of one of the longer sides of rectangle 38.

As best seen in FIG. 1A, an exemplary embodiment of plate 10 is divided into tail portion 40 and head portion 42. Tail portion 40 has a single "row" of holes 14, illustrated as six holes in FIG. 1. Tail portion 40 forms a non-periprosthetic zone, in that holes 14 in tail portion 40 are positioned and oriented to attach to a bone without a prosthesis therein. Head portion 42 has multiple subsets 44 of holes 14, with each subset 44 comprising three holes arranged diagonally with respect to longitudinal axis 46 of plate 10. Head portion 42 forms a periprosthetic zone, in that holes 14 in head portion 42 are positioned and oriented to attach to a bone with a prosthesis therein.

Figure 4:
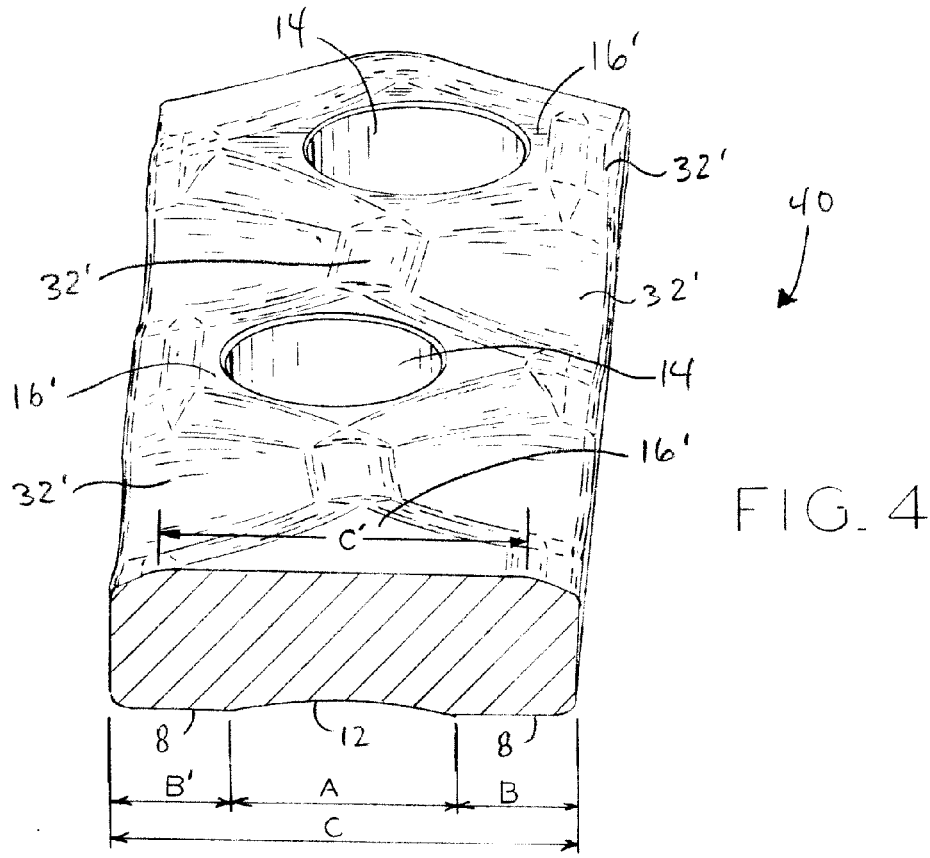
FIG. 4 is a perspective, cross-sectional view of the plate shown in FIG. 1, illustrating a tail portion of the plate.
Figure 5:
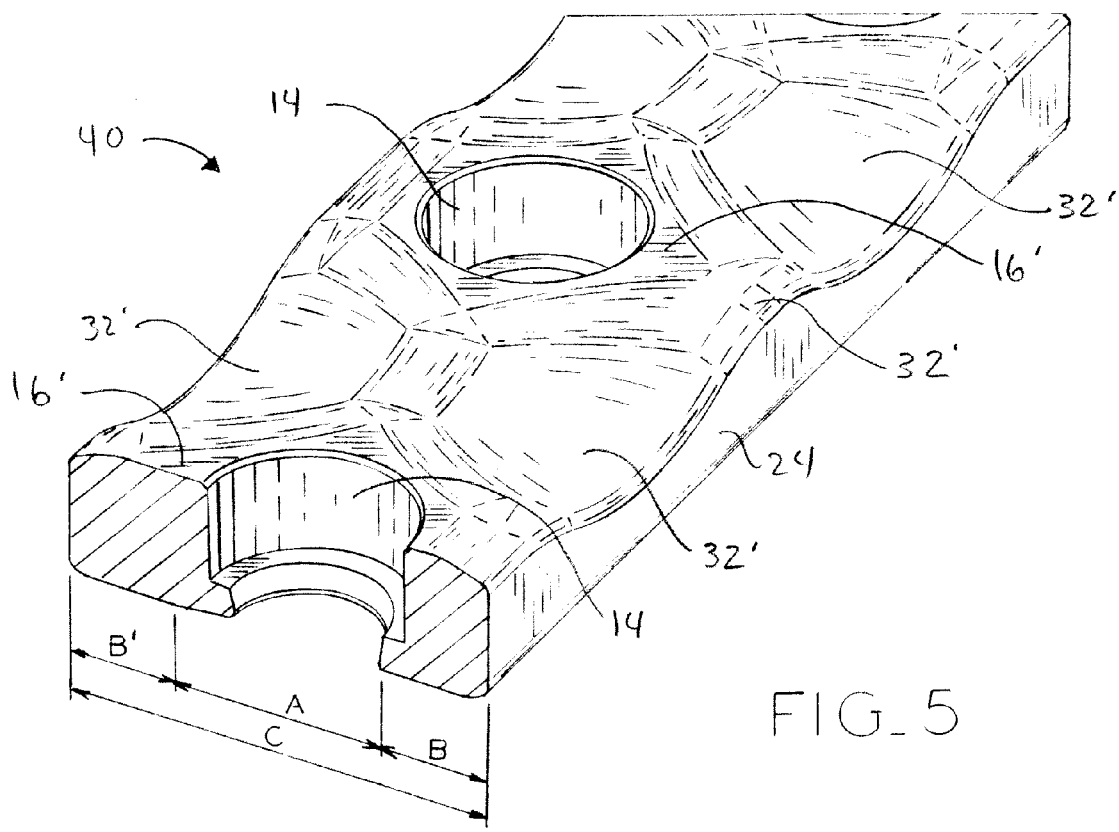
FIG. 5 is a perspective, cross-sectional view of the plate shown in FIG. 1, illustrating a tail portion of the plate.

Referring generally to FIGS. 4 and 5, cross sectional views of plate 10 illustrate linearly shaped portions 8 extending across a lateral extent of plate 10. Tail portion 40 has bone facing surface 4 with overall width C, which includes linear portions 8 having linear portion widths B, B' and non-linear portion 12 having non-linear width A. Linear widths B, B' may be equal or unequal, and width B may vary with respect to the width of B' at various points along the longitudinal extent of bone facing surface 4. Linear portion widths B and B' combine to form as little as about 35%, 45% or 50% of overall width C and as much as about 80%, 90% or 100% of overall width C, or within any ranged defined by any of the foregoing values. In the illustrated embodiment of FIGS. 4 and 5, for example, linear portion widths B, B' comprise about 51% of overall width C.

Referring now to FIG. 1B, linear portions 8' may also be described as covering a portion of the total area of top surface 2 in both tail portion 40 and head portion 42. Linear or planar portions 8' correspond with linear lateral portions 8, described above (FIG. 2). The combined area of coverage of both of linear portions 8' on bottom surface 4, expressed as a percentage of the overall area of bottom surface 2, may form as little as 35%, 45% or 50% and as much as 80%, 90% or 100%, or within any ranged defined by any of the foregoing values. In the illustrated embodiment of FIG. 1B, for example, linear portions 8' combine to comprise about 50% of the overall area of bottom portion 4.

Turning now to FIG. 6, head portion 42 is shown with bone facing surface 4 having overall width Z as measured across the widest point of each proximate scallop in side walls 22, 24. Overall width Z includes linear portions 8 having widths Y, Y' and non-linear portion 12 having width X. Similar to linear portion widths B, B', linear portion widths Y, Y' may have equal or unequal widths and may vary with respect to one another across the longitudinal extent of plate 10. Linear portion widths Y, Y' of linear portions 8 may combine to form as little as about 24%, 34% or 44% of overall width Z and as much as about 60%, 70% or 80% of overall width Z, or within any ranged defined by any of the foregoing values. In the illustrated embodiment of FIG. 6, for example, linear portion widths Y, Y' comprise about 68% of overall width Z.

Referring to FIG. 2, top surface 2 of bone treatment plate 10 is of generally convex shape. More particularly, as shown in the cross-section of FIG. 2, top surface 2 defines a generally linearly shaped middle portion 16 which is essentially parallel to the generally linearly shaped lateral portions 8 of second surface 4 and defines a part of the other longer side of the rectangle 38. The generally non-linearly shaped lateral portions 32 (FIG. 2) form part of a circumference of a circle, i.e. the non-linearly shaped portions 32 are curved, namely in the shape of a circular arc. Non-linearly shaped portions 32 of top surface 2 and non-linearly shaped middle portion 12 of bottom surface 4 (discussed above) cooperate to define a generally U-shaped cross-sectional profile of plate 10. In the illustrated embodiment, this U-shaped cross-sectional profile extends across substantially all of plate 10. However, it is within the scope of the present disclosure that only a portion of plate 10 may have a U-shaped cross-sectional profile, such as where either top face 2 or bottom face 4 lacks a non-linearly shaped portion.

Referring still to FIG. 2, the horizontal line dissecting plate 10 describes plane 36, which is parallel to the generally linearly shaped middle portion 16 and the generally linearly shaped lateral portions 8 of plate 10. Vertical line intersecting plane 36 is normal 34, and the points of intersection of normal 34 with plate 10 describe geometric plate centers 18, 20. The thickness of plate 10 is defined as the separation between center 18 and center 20, i.e. the thickness of plate 10 is the separation between the substantially parallel linearly shaped portions of the first and second surfaces. The thickness of plate 10 can be advantageously varied to accommodate the size of the bone fracture to be treated, and/or the size of the bone in question. Moreover, the thickness of plate 10 can vary along its length.

Returning to FIG. 6, top surface 2 has a substantially continuous linear (i.e., flat or planar) portion 16' across the extent of head portion 42. By way of illustration, a marking instrument could hypothetically be used to draw a line across substantially the entire longitudinal extent of head portion 42 of plate 10 without removing the marking instrument from linear portion 16' of top surface 2. For purposes of this illustration, the openings in top surface 2 created by holes 14 are considered to form a part of linear portion 16' because each such opening defines a substantially planar region.

Top surface 2 has overall width Z in head portion 42, with linear portion 16' defining a linear portion width Z' in head portion 42 as shown in FIG. 6. Linear portion width Z' may form as little as about 36%, 41% or 46% of overall width Z and as much as about 50%, 55% or 60% of overall width Z, or within any range defined by any of the foregoing values. In the illustrated embodiment of FIG. 6, for example, linear portion width Z' comprises about 45% of overall width Z.

Referring now to FIGS. 4-5, linear portions 16' in tail portion 40 are interrupted by non-linear portions 32', so that it would not be possible to draw a continuous line across the entire longitudinal extent of tail portion 40 without contacting at least one of non-linear portions 32'.

Top surface 2 has overall width C in tail portion 40, with linear portion 16' defining a linear portion width C' in tail portion 40 as shown in FIG. 4. Linear portion width C' may form as little as about 52%, 57% or 62% of overall width Z, and as much as about 77%, 82% and 87% of overall width Z, or within any range defined by any of the foregoing values. In the illustrated embodiment of FIG. 4, for example, linear portion width C' comprises about 77% of overall width C.

Moreover, because widths C', Z' of linear portion 16' vary depending on the particular chosen cross-section of plate 10, linear portion 16' may also be described as covering a portion of the total area of top surface 2 in both tail portion 40 and head portion 42. The area of coverage of linear portion 16' in tail portion 40, expressed as a percentage of the overall area of top surface 2 in tail portion 40, may form as little as 8%, 12% or 16% and as much as 24%, 28% or 32%, or within any range defined by any of the foregoing values. In the illustrated embodiment of FIG. 1A, for example, linear portion 16' comprises about 20% of the overall area of top surface 2 in tail portion 40.

Referring still to FIG. 1A, linear portion 16' occupies a greater percentage of the total surface area in head portion 42 of plate 10. The area of coverage of linear portion 16' in head portion 42, expressed as a percentage of the overall area of top surface 2 in head portion 42, may form as little as 20%, 25% or 30% and as much as 40%, 45% or 50%, or within any ranged defined by any of the foregoing values. In the illustrated embodiment of FIG. 1A, for example, linear portion 16' comprises about 35% of the overall area of top surface 2 in head portion 42.

Referring now to FIG. 1B, bottom surface 4 also has linear or planar portions 8' corresponding with linear lateral portions 8 (FIG. 2). The area of coverage of both of linear portions 8' on bottom surface 4, expressed as a percentage of the overall area of bottom surface 2, may form as little as 30%, 35% or 40% and as much as 80%, 65% or 70%, or within any ranged defined by any of the foregoing values.

Plate 10 of FIG. 1 does not explicitly show a plate having first surface 2 and second surface 4 which run exactly parallel to one another for the longitudinal extent of plate 10, but plane 36 of plate 10 is essentially parallel to the bone surface to which plate 10 is to be attached, i.e. plane 36 of plate 10 is essentially parallel to bone surface 6, independent of the exact shape of bone surface 6 and the exact shape of plate 10.

In this respect it should be noted, that the width of plate 10 is defined by the separation between the centers of side walls 22, 24 of plate 10, and that the width of plate 10 is also adapted to correspond with the contour of bone surface 6. It should also be noted that side walls 22, 24 need not necessarily be perpendicular to the generally planar outer sections 8 or the generally linearly shaped middle portions 16, nor do side walls 22, 24 have to be linear in shape, but can also be convex or concave. However, the fact that the generally linearly shaped middle portion 16 and the generally linearly shaped lateral portions 8 are parallel to one another still permit the bone healing plate 10 of the present disclosure to be described as having a generally rectangular cross-section, with the generally linearly shaped lateral portions 8 and the generally linearly shaped middle portion 16 forming parts of the longer sides of the rectangle 38.

Moreover, a length of plate 10 can be defined by the separation between the geometric centers of end walls 26, 28 (see FIG. 3) of plate 10 and, likewise, the length of the plate is adapted to correspond with the size of the fracture of the bone surface, and/or the size of the bone in question. As best seen in FIG. 1A, plate 10 has a curved overall shape as viewed from top surface 2. The body of plate 10 defines a central line or longitudinal "axis" 46 running through the extent of plate 10, in which axis 46 is curved or non-linear. As a result of this curvature of axis 46, head portion 42 is oblique relative to tail portion 40 when viewed from top surface 2. This curvature may, for example, facilitate the use of a universal jig for different lengths of bone plate 10, such as the jig described in a U.S. patent application Ser. No. 12/683,953 filed on even date herewith entitled BONE PLATE FIXATION SYSTEM, the disclosure of which is hereby incorporated herein by reference in its entirety.

The cross-section of plate 10 shown in FIG. 2 can be the cross-section of distal femur plate 10 shown in FIG. 1. As the diameter of the thigh bone varies along the length of the bone, so will both the width of plate 10 and the radius of curvature of the non-linearly shaped middle portion 12 vary, with the amount of variation depending on the variation in bone size of the femur. For example, the radius of curvature of the non-linearly shaped middle portion 12 of distal femur plate 10 varies along the contour of bone surface 6. However, the non-linearly shaped middle portion 12 will generally be at the center of plate 10, and viewed from below (not shown here) will look like a groove generally following the contour of bone surface 6. For example, for curved bones, plate 10 will also be curved.

The width of plate 10 is approximately 2 to 20 times larger than the diameter of hole 14, and the thickness of plate 10 is approximately ½ to 18 times the diameter of hole 14. The material of plate 10 can be any material typically used in osteosynthetic surgical procedures and be selected from the group including titanium, surgical steel, surgical synthetic materials, composite synthetic polymeric materials or even biodegradable surgical materials.

As can be seen in FIG. 1, plate 10 is of a substantially elongated shape, i.e. plate 10 extends longitudinally essentially from the top left of FIG. 1 to the bottom right of FIG. 1. Along this longitudinal extent, i.e. along the length of plate 10, the cross section of plate 10, as described herein and as shown in FIG. 2, is generally perpendicular to the longitudinal extent.

If one were to make several sectional illustrations along the longitudinal extent of plate 10, then in many of the sectional illustrations, such as the majority or substantially every sectional illustration, at least one of first and second surfaces 2, 4 would define at least one generally linearly shaped portion 8, 16. This does not exclude the existence of cross sections perpendicular to the longitudinal extent in which—due to the specific design of the plate—neither of the first or second surfaces 2, 4 have a generally linearly shaped portion 8, 16 at a portion of the plate, for example, in the region of holes 14.

As can be seen in FIG. 1 plate 10 is generally curved along its longitudinal extent, i.e. the longitudinal extent of plate 10 is non-linearly shaped. In other words, due to the shaped contour of the bone surface, a "center axis" of plate 10 is a curve rather than a straight line.

FIG. 2 also shows hole 14 extending from top surface 2 to bone facing surface 4 which is adapted for use with bone screws, i.e. the shape and geometry of hole 14 can be varied in accordance with the type of bone screw used to attach plate 10 to bone surface 6. Thus, plate 10 is in no way limited to any particular type of bone screw. It is within the scope of the present invention that the plate may be fixed to the bone by bone screws such that the plate has no or only small contact with the bone surface, i.e. the plate is not screwed against the bone surface.

In the embodiment illustrated in FIG. 2, the non-linearly shaped middle portion 12 has a curved shape. However, in the context of the present disclosure, this can also be a triangular middle portion, a rectangular middle portion or generally any kind of concave or concave-like middle portion, such as to reduce the manufacturing demands for the plate.

Plate 10 of FIG. 2 has a generally rectangular cross section as is illustrated by rectangle 38. A boundary or periphery of the cross section of plate 10 defines the longer sides of rectangle 38 within which the boundary of the cross section is inscribed, i.e. first and second surfaces 2, 4 of plate 10 define the size (height or thickness) of rectangle 38. As can be seen in FIG. 2, the non-linearly shaped middle portion 12 defined by second surface 4 lies within rectangle 38 and is positioned between two generally linearly shaped lateral portions 8 forming a part of one of the longer sides of rectangle 38 and first surface 2 defines middle portion 16 which forms a part of the other longer side of rectangle 38. Middle portion 16 is positioned between two lateral portions 32 lying inside rectangle 38.

The non-linearly shaped portion 12 is a generally convex part of the boundary of the cross section of plate 10, and the non-linearly shaped parts 32 are generally concave parts of the boundary. As can be seen from rectangle 38 of FIG. 2, generally linearly shaped middle portion 16 of first surface 2 is essentially parallel to generally linearly shaped lateral portions 8 of second surface 4. Lateral portions 32 of FIG. 2 are of curved shape but could also be linearly shaped.

Figure 3:
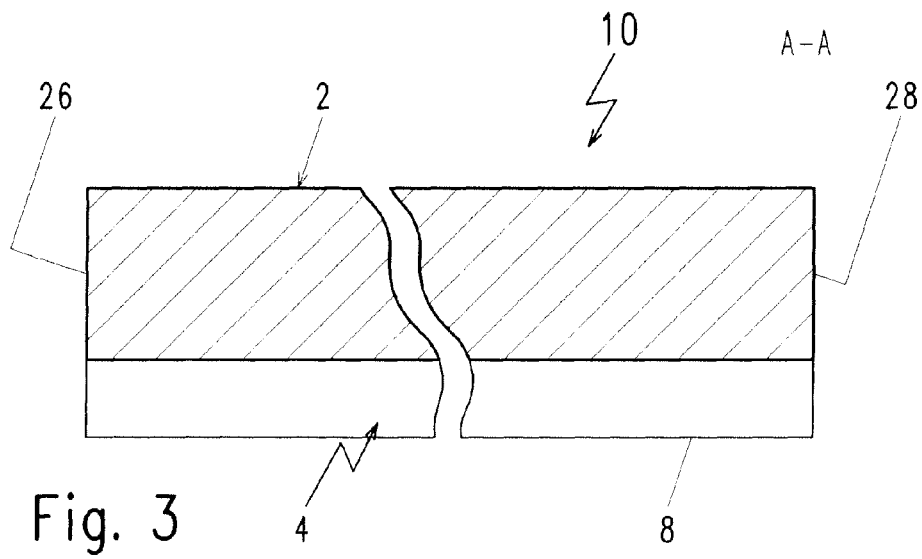
FIG. 3 shows a section of the plate shown in FIG. 2, along the line AA.

FIG. 3 shows section A-A along the normal 34 of FIG. 2. Section A-A of plate 10 of FIG. 3 shows end walls 26, 28 of plate 10, connecting first surface 2 and second surface 4 of plate 10 which, in this example, forms a rectangle.

If required, a plurality of grooves may be provided along the generally non-linearly shaped middle portion 12 of FIG. 2. If provided, these grooves can achieve a reduction in the contact area between plate 10 and bone surface 6.

The structure of the surface of the generally non-linearly shaped middle portion 12 can include any type of geometry which is beneficial for the healing process of the bone.

Furthermore, non-linearly shaped portions 12, 32 can be of any geometric shape, i.e. a straight line, a curve, a saw tooth shaped portion etc. It should be noted, however, that this geometric shape does not lie in the same plane as the linearly shaped portions, but rather intersects this plane.

Moreover, the point of transition between linearly shaped middle portion 16 of the first surface 2 and each of the two lateral portions 32 (non-linearly shaped portions 32) can be defined by a change of the radius of curvature or by a change of the gradient (slope) of first surface 2. Should lateral portions 32 be substantially straight lines intersecting the substantially straight line of middle portion 16, then there is a kink at the point where the two lines meet.

One could consider providing the surface of linearly middle portion 16 with a slight curve, with lateral portions 32 then also being curved but having a different radius of curvature, hence a change of the radius occurs at the transition between the two curved portions.

The description of the disclosure is merely exemplary in nature, and, thus, variations do not depart in the gist of the disclosure are intended to be within the scope of the disclosure. Such variations are not to be regarded as a departure from the spirit in the scope of the disclosure.

LIST OF REFERENCE NUMERALS 2 first surface
4 second surface
6 bone surface
8 lateral portion
10 plate
12 middle portion
14 hole
16 middle portion
18 center
20 center
22 side wall
24 side wall
26 end wall
28 end wall
32 lateral portion
34 normal
36 plane
38 rectangle

What is claimed is:

1. A plate for the treatment of bone fractures, the plate comprising:
    an elongated body having a length defining a central longitudinal axis,
    a width defining a maximum extent of the plate transverse to the central longitudinal axis,
    a top surface including a linear top segment, defining a top surface plane, and a first convexly curved lateral segment and a second convexly curved lateral segment, the first convexly curved lateral segment and the second convexly curved lateral segment disposed on opposing sides of the linear top segment,
    a bone facing surface opposite the top surface, the bone facing surface comprising and a first linear bone-facing segment and a second linear bone-facing segment extending the length of the plate, the first linear bone-facing segment and the second linear bone-facing segment disposed parallel to the linear top segment, and at least one non-linear bone-facing segment disposed between the first linear bone-facing segment and the second linear bone-facing segment, and
    a first side and a second side opposing one another and joined directly to, respectively, the first convexly curved lateral segment and the second convexly curved lateral segment to interconnect the top surface and the bone facing surface,
    wherein a plurality of cross sections taken transverse to the central longitudinal axis each define a generally rectangular boundary enclosing the entire plate cross section, the linear top segment forming part of a first long side of the rectangular boundary, the first linear bone-facing segment and the second linear bone-facing segment forming part of a second long side of the rectangular boundary, the first side and the second side of the plate forming, respectively, part of a first side and part of a second side of the rectangular boundary.

2. The plate of claim 1, wherein, in each one of the plurality of cross sections, the linear top segment comprises between 36% and 87% of the width of the plate.

3. The plate of claim 1, wherein, in each one of the plurality of cross sections, the first linear bone-facing segment and the second linear bone-facing segment together comprise between 24% and 100% of the width of the plate.

4. The plate of claim 1, further comprising a head portion and a tail portion opposite the head portion.

5. The plate of claim 4, wherein, in each one of the plurality of cross sections taken in the tail portion, the linear top segment comprises between 52% and 87% of the width of the plate.

6. The plate of claim 4, wherein, in each one of the plurality of cross sections taken in the head portion, the linear top segment comprises between 36% and 60% of the width of the plate.

7. The plate of claim 4, wherein, in each one of the plurality of cross sections taken in the head portion, the first linear bone-facing segment and the second linear bone-facing segment together comprise between 24% and 80% of the width of the plate.

8. The plate of claim 4, wherein, in each one of the plurality of cross sections taken in the tail portion, the first linear bone-facing segment and the second linear bone-facing segment together comprise between 35% and 100% of the width of the plate.

9. The plate of claim 1, wherein, in each one of the plurality of cross sections the first linear bone-facing segment and the second linear bone-facing segment are joined to respective first side and second side of the plate to form a first corner and a second corner of the rectangular boundary.

10. The plate of claim 1, wherein the linear top segment has a width, transverse to the central longitudinal axis, varying along the length of the plate.

11. The plate of claim 1, wherein the at least one non-linear bone-facing segment has a width, transverse to the central longitudinal axis, varying along the length of the plate.

12. The plate of claim 1, wherein, the plate has a thickness along the central longitudinal axis, the thickness varying along the length of the plate.

13. The plate of claim 1, wherein the at least one non-linear bone-facing segment is disposed along the central longitudinal axis.

14. The plate of claim 1, wherein each of the first linear bone-facing segment and the second linear bone-facing segment is adjacent to the at least one non-linear bone-facing segment.

15. The plate of claim 1, wherein the at least one non-linear bone-facing segment defines a concave region within the rectangular boundary of each one of the plurality of cross sections.

16. The plate of claim 1, wherein the at least one non-linear bone-facing segment is curved in the shape of a circular arc.

17. The plate claim 16, wherein the radius of curvature of the circular arc varies along the length of the plate.

18. The plate of claim 1, wherein the at least one non-linear bone-facing segment is adapted to be matched to a contour of the bone surface.

19. The plate of claim 1, wherein in each one of the plurality of cross sections the top surface has an overall convex shape.

20. The plate of claim 1, wherein, in each one of the plurality of cross sections, the linear top segment is disposed along the central longitudinal axis.

21. The plate of claim 1, wherein, in each one of the plurality of cross sections, the linear top segment is bordered on each side by a linear lateral segment extending at angle from the linear top segment.

22. The plate of claim 1, further comprising a head portion and a tail portion opposite the head portion, the head portion oblique relative to the tail portion.

23. The plate of claim 1, wherein the central longitudinal axis is non-linear.

24. The plate of claim 1, further comprising at least one hole configured to receive a bone screw, the at least one hole extending between the top surface and the bone facing surface.

\* \* \* \* \*